United States Patent [19]
Willingham et al.

[11] Patent Number: 5,855,654
[45] Date of Patent: Jan. 5, 1999

[54] PYRIDAZINONES AS MARINE ANTIFOULING AGENTS

[75] Inventors: Gary Lewis Willingham, Glenside, Pa.; Samuel Eugene Sherba, Willingboro, N.J.; Barry Clifford Lange, Lansdale; Enrique Luis Michelotti, Fort Washington, both of Pa.

[73] Assignee: Rohm and Haas Company, Philadelphia, Pa.

[21] Appl. No.: 987,081

[22] Filed: Dec. 9, 1997

Related U.S. Application Data

[60] Provisional application No. 60/036,527, Jan. 30, 1997.

[51] Int. Cl.$^6$ .............................. A01N 43/58; C09D 5/16; C09D 5/14

[52] U.S. Cl. .................. 106/18.32; 106/18.3; 106/18.33; 106/18.34; 106/18.35; 424/78.01; 424/405; 424/630; 514/64; 514/241; 514/247; 514/248; 514/252; 514/345; 514/372; 514/396; 514/417; 514/479; 514/493; 514/494; 514/500; 514/595; 514/600; 514/706; 514/709; 523/122; 523/179

[58] Field of Search .................. 106/18.32, 18.3, 106/18.33, 18.34, 18.35; 514/247, 248, 252, 64, 241, 345, 372, 396, 417, 479, 493, 494, 500, 595, 600, 706, 709; 424/78.09, 405, 630; 427/384, 385.5, 388.1, 393, 393.5, 393.6, 392; 523/122, 179

[56] References Cited

U.S. PATENT DOCUMENTS

| 5,488,051 | 1/1996 | Romer et al. ............................ 514/248 |
| 5,741,793 | 4/1998 | Young et al. ............................ 514/247 |

OTHER PUBLICATIONS

Chemical Abstract No. 93:181042 which is an abstract of Japanese Patent Specification No. 55–089205, Jul. 1980.

*Primary Examiner*—Anthony Green
*Attorney, Agent, or Firm*—S. Matthew Cairns

[57] ABSTRACT

Disclosed is a method of inhibiting the growth of marine organisms on a marine structure, by applying dihydropyridazinone and pyridazinone compounds onto or into the marine structure. These compounds may be directly incorporated into the marine structure during manufacture, directly applied to the structure, or applied to the structure by means of a coating.

7 Claims, No Drawings

PYRIDAZINONES AS MARINE ANTIFOULING AGENTS

This is a nonprovisional application of prior pending provisional application Ser. No. 60/036,527 filed Jan. 30, 1997.

BACKGROUND OF THE INVENTION

This invention relates generally to a method of inhibiting the growth of organisms on a marine structure. In particular, this invention relates to the use of dihydropyridazinone and pyridazinone compounds as marine antifouling agents.

Marine antifouling agents are used commercially to prevent growth of organisms on marine structures. Tributyltin oxide and other organotins have been the major marine antifouling agents in use for many years. There is currently much concern over the effects of tin on marine environments. For example, high levels of tin in harbor waters have been linked to shell deformation in some bivalve species, such as oysters.

Some organic compounds have been suggested as marine antifouling agents. For example, U.S. Pat. No. 5,071,479 (Gruening) discloses the use of 3-iodopropargyl N-butyl carbamate as a marine antifouling agent. These types of compounds have not achieved commercial prominence because they do not meet the same performance requirements as tin based antifouling agents.

EP 478195 (Egan, et al.) discloses certain dihydropyridazinone and pyridazinone compounds as medical and agrochemical fungicides. EP 478195 also discloses these compounds to be useful as wood preservatives effective against wood decay organisms. Such wood decay organisms are fungi. There is no disclosure of these compounds as marine antifouling agents.

The organisms controlled by agricultural fungicides or wood preservatives are very different from those controlled by marine antifouling agents. Marine antifouling agents control multicellular organisms and slime, such as diatoms, barnacles, hydroids, grassy brown felt algae, and the like. The effectiveness of agrochemical fungicides useful in combating fungi on plants cannot be used to predict the effectiveness of these compounds as marine antifouling agents in sea water and brackish water.

The problem addressed by this invention is to provide marine antifouling agents having increased performance and little or no harmful effects on marine environments.

STATEMENT OF THE INVENTION

The present invention provides a method of inhibiting the growth of marine organisms on a marine structure, comprising applying to, on, or in any marine structure, article, or composition in contact with or intended for contact with sea or brackish water an effective amount of a marine antifouling agent of formula:

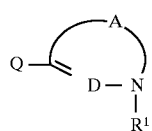
(I)

wherein:
A=—(CHR²)ₙ—CHR⁷—Z—, —(CHR²)ₙ—O—Z—, —(CHR²)ₙ—S—Z—, —O—CHR⁷—Z—, —CR²=CR⁷—Z—, CR²=N—Z—, —CHR²—CR⁷=X, —CR²=CR⁷—X=, or —S—CHR⁷—Z—;

D=CR² or nitrogen;
Q=an aromatic group selected from

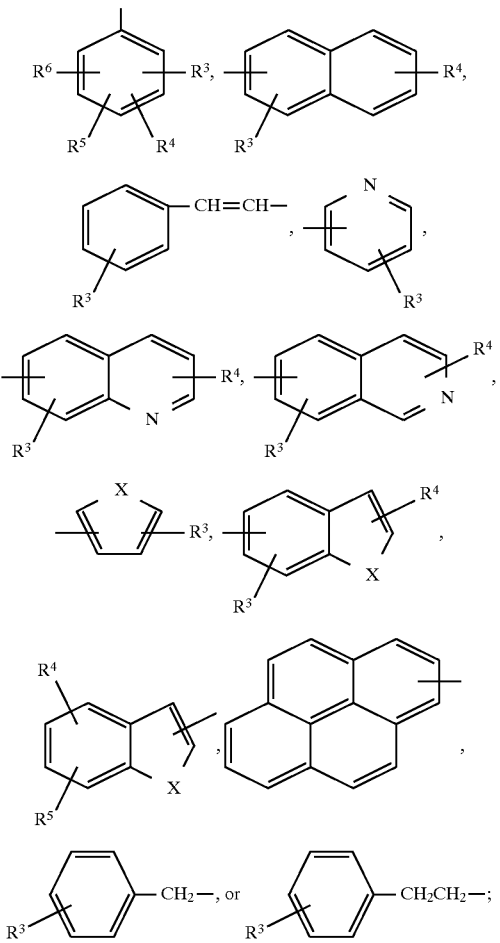

Z=carbonyl or thiocarbonyl;
X=carbon substituted by halogen, alkoxy, alkynylthio, or triazolyl;
R¹=alkyl, hydroxyalkyl, cyanoalkyl, cycloalkylalkyl, heterocyclylalkyl, phenyl, phenylalkyl, phenylcarbonyl, alkenyl, haloalkenyl, phenylalkenyl, alkynylalkenyl, alkynyl, haloalkynyl, phenylalkynyl, heterocyclyl, dialkynyl, heterocyclylalkynyl, cycloalkylalkynyl, alkenylalkynyl, hydroxyalkynyl, alkoxyalkynyl, alkanoyloxyalkynyl, formylalkynyl, trialkylsilylalkynyl, haloalkenylalkynyl, carboxyalkynyl, or alkoxycarbonylalkynyl;
R²=H, (C₁–C₃)alkyl, phenyl, or halogen;
R³ and R⁶ are independently H, alkoxy, or halogen;
R² and R³ may together form a (C₁–C₃)alkyl, (C₂–C₃) alkylene, or carbonyl link;
R⁴=H, halogen, alkoxy, or nitro;
R⁵=H, halogen, alkoxy, nitro, alkyl, alkylthio, haloalkyl, haloalkoxy, haloalkylthio, phenyl, phenoxy, or cyano;
R⁷=H, (C₁–C₃)alkyl, phenyl, halogen, alkynylalkenyl, alkynyl, dialkynyl, haloalkynyl, or alkenylalkynyl;
R⁷ and R² may together form a fused phenyl ring; and
n=0, 1, or 2.

It is a further object of the invention to provide a method of controlling or inhibiting the growth of microorganisms in a locus comprising introducing into or onto the locus to be protected an effective amount of a microbicide of formula (I), as defined above.

DETAILED DESCRIPTION OF THE INVENTION

As used herein, "marine antifouling agents" include algaecides and molluscicides. "Marine antifoulant activity" is intended to include both the elimination of and inhibition or prevention of growth of marine organisms. Marine organisms controlled by the marine antifouling agents suitable for use in this invention include both hard and soft fouling organisms. Generally speaking, the term "soft fouling organisms" refers to plants and invertebrates, such as slime, algae, kelp, soft corals, tunicates, hydroids, sponges, and anemones and the term "hard fouling organisms" refers to invertebrates having some type of hard outer shell, such as barnacles, tubeworms and mollusks.

As used in this specification, "alkyl" means straight chain, branched, cyclic, or any combination thereof; "halogen" means fluorine, chlorine, bromine, or iodine; and all amounts are percent by weight ("% wt"), unless otherwise noted. All % wt ranges are inclusive. As used herein, the following abbreviations are applied: mL=milliliter, μL=microliter, g=grams, μg/mL=micrograms per milliliter, ppm=parts per million, mm=millimeter, nm=nanometer, μm=micrometer, DMSO=dimethyl sulfoxide, DMF=dimethylformamide, ASTM=American Society for Testing and Materials, and Abs=absorbance.

As used herein, "microbicide" refers both to a compound capable of inhibiting or controlling the growth of microorganisms in a locus. The term "microorganism" includes, but is not limited to, fungi, bacteria, and algae.

The compounds useful as marine antifouling agents and microbicides are those of formula (I), above. Preferred compounds are those wherein:

A=—$(CHR^2)_n$—$CHR^7$—Z; —$CR^2$=$CR^7$—Z—; $CHR^2$—$CR^7$=X—; or —$CR^2$=$CR^2$—X—;
D=nitrogen;
Q=an aromatic group selected from:

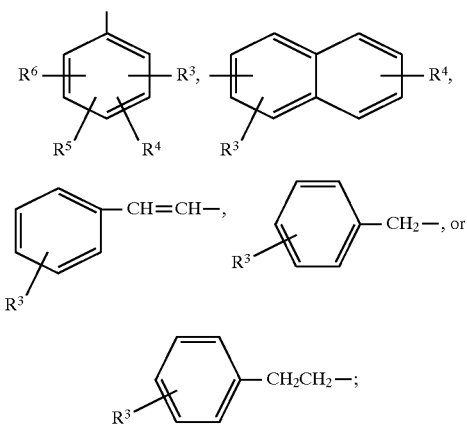

Z=a carbonyl or thiocarbonyl; X=a carbon substituted by halo, alkoxy, alkynylthio, or triazolyl;
$R^1$=$(C_3$–$C_{10})$alkynyl, $(C_4$–$C_{20})$dialkynyl, halo$(C_3$–$C_6)$ alkynyl, phenyl$(C_3$–$C_6)$alkynyl, heterocyclyl$(C_3$–$C_6)$ alkynyl, $(C_3$–$C_6)$cycloalkyl$(C_3$–$C_6)$alkynyl, $(C_3$–$C_6)$ alkenyl$(C_3$–$C_6)$alkynyl, hydroxy$(C_3$–$C_6)$alkynyl, $(C_1$–$C_6)$alkoxy$(C_3$–$C_6)$alkynyl, $(C_1$–$C_6)$alkanoyloxy $(C_3$–$C_6)$alkynyl, formyl$(C_3$–$C_6)$alkynyl, tri$(C_1$–$C_6)$ alkylsilyl$(C_3$–$C_6)$alkynyl, halo$(C_3$–$C_6)$alkenyl$(C_3$–$C_6)$ alkynyl, carboxy$(C_3$–$C_6)$alkynyl, $(C_1$–$C_6)$ alkoxycarbonyl$(C_3$–$C_6)$alkynyl;
$R^2$=hydrogen, $(C_1$—$C_3)$alkyl, phenyl, or halogen;
$R^3$ and $R^6$ are independently hydrogen, $(C_1$–$C_6)$alkoxy, or halogen;
$R^2$ and $R^3$ may together form a $(C_1$–$C_3)$alkyl;
$R^4$=hydrogen, halogen, $(C_1$–$C_6)$alkoxy, or nitro;
$R^5$=hydrogen, halogen, nitro, $(C_1$–$C_6)$alkyl, $(C_1$–$C_6)$ alkoxy, $(C_1$–$C_6)$alkylthio, halo$(C_1$–$C_6)$alkyl, halo $(C_1$–$C_6)$alkoxy, halo$(C_1$–$C_6)$alkylthio, phenyl, phenoxy, or cyano;
$R^7$=hydrogen, $(C_1$–$C_3)$alkyl, phenyl, halogen, $(C_3$–$C_6)$ alkynyl$(C_2$–$C_6)$alkenyl, $(C_3$–$C_{10})$alkynyl, $(C_4$–$C_{20})$ dialkynyl, halo$(C_3$–$C_6)$alkynyl, or $(C_3$–$C_6)$alkenyl $(C_3$–$C_6)$alkynyl;
$R^2$ and $R^7$ may together form a fused phenyl ring; and n=1.

Especially preferred compounds include those wherein $R^1$ is $(C_3$–$C_{10})$alkynyl, halo$(C_3$–$C_6)$alkynyl, or $(C_3$–$C_6)$alkenyl $(C_3$–$C_6)$alkynyl.

Examples of preferred compounds of the present invention include the compounds listed in the table below.

| No. | Compound Name |
|---|---|
| 1 | 6-(4-chlorophenyl)-2-(2'-pentynyl)pyridazin-3-one |
| 2 | 6-(4-chlorophenyl)-2-(2'-pentynyl)-4,5-dihydropyridazin-3-one |
| 3 | 6-(4-chlorophenyl)-2-(3'-vinyl-2'-propynyl)pyridazin-3-one |
| 4 | 7-chloro-2,4,4a,5-tetrahydro-2-(2-pentyn-1-yl)-indeno[1,2-c]-pyridazin-3-one |
| 5 | 6-(3-fluoro-4-chlorophenyl)-2-(2'-pentynyl)pyridazin-3-one |
| 6 | 6-(4-chlorophenyl)-2-(5'-fluoro-2'-pentynyl)pyridazin-3-one |

Preparation of the compounds of the present invention are known in the literature. For example, the synthesis of the compounds useful in this invention can be found in EP 478195 (Egan et al.), which is hereby incorporated by reference. In addition, the dihydropyridazinones of the present invention can be prepared by a two step sequence starting from an arylketo acid or ester of formula:

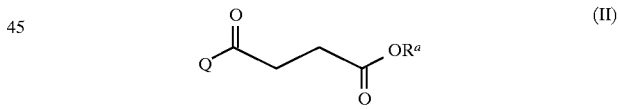

wherein Q is as defined in formula (I) above, and $R^a$ is hydrogen or alkyl.

Compounds of formula (II) can be reacted with about an equivalent of hydrazine or a substituted hydrazine having the formula $H_2NNHR^b$ wherein $R^b$ is hydrogen or alkyl to yield compounds of formula:

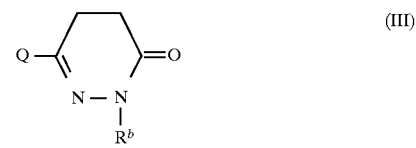

Examples of suitable solvents for this reaction include alcohols, such as ethanol, n-propanol, or n-butanol. The reaction is generally carried out at atmospheric pressure at a temperature of –10° to 200 ° C., preferably 25° to 150 ° C.

The compounds of formula (III) wherein $R^b$ is hydrogen can then be alkylated using the appropriate alkylating agent, for example an alkynyl mesylate or alkynyl halide, by a standard N-alkylating procedure to obtain the desired dihydropyridazinone. Standard N-alkylating procedures suitable for this reaction include, for example, the use sodium hydride in an aprotic polar solvent such as DMF or the use of a phase transfer catalyst such as tetrabutylammonium hydrogen sulfate. The reaction is generally carried out at a temperature of −10° to 250° C., preferably 20° to 100° C.

The marine antifouling agents of the present invention can be used to inhibit the growth of marine organisms by application of an effective amount of one or more of the marine antifouling agents onto or into a marine structure. Depending upon the particular marine structure to be protected, the marine antifouling agents of the present invention can be directly incorporated into the marine structure, applied directly to the marine structure, or incorporated into a coating which is then applied to the marine structure.

Suitable structures include, but are not limited to: boats, ships, oil platforms, piers, pilings, docks, elastomeric rubbers, and fish nets. The marine antifouling agents of the present invention are typically directly incorporated into structures such as elastomeric rubber or fish net fibers during manufacture. Direct application of the compounds of the invention is typically made to structures such as fish nets or wood pilings. The compounds of the invention can also be incorporated into a marine coating, such as a marine paint or varnish.

In general, the amount of marine antifouling agent necessary to inhibit or prevent the growth of marine organisms is from 0.1 to 30% wt based on the weight of the structure to be protected or based on the weight of the coating to be applied. When the marine antifouling agents of the invention are directly incorporated into or directly applied onto a structure, the amount of the antifouling agent suitable to inhibit the growth of marine organisms is generally from 0.1 to 30% wt based on the weight of the structure. It is preferred to use an amount from 0.5 to 20% wt; more preferably, from 1 to 15% wt. When incorporated into a coating, the amount of marine antifouling agent suitable to inhibit the growth of marine organisms is generally from 0.1 to 30% wt based on the weight of said coating. The amount of marine antifouling agent is preferably from 0.5 to 15% wt; more preferably, from 1 to 10% wt.

If one of the marine antifouling agents of the invention is to be combined with a second marine antifouling agent, the ratio of the first marine antifouling agent to the second marine antifouling agent is from 99:1 to 1:99; preferably, from 75:25 to 25:75. The total of the combined marine antifouling agents necessary to inhibit or prevent the growth of marine organisms is from 0.1 to 30% wt based on the weight of the structure to be protected or the weight of the coating to be applied.

In general, the marine antifouling agents of the invention are incorporated in a carrier such as water; organic solvent, such as xylene, methyl isobutyl ketone, and methyl isoamyl ketone; or mixtures thereof.

Direct applications of the marine antifouling agents of the invention may be by any conventional means, such as dipping, spraying, or coating. Fish nets, for example, may be also protected by dipping the fish nets into a composition comprising one or more of the compounds of the invention and a carrier or by spraying the fish nets with said composition.

Structures such as wood pilings and fish nets may be protected by directly incorporating the marine antifouling agents into the structure. For example, a composition comprising one or more marine antifouling agents in a carrier may be applied to wood used for pilings by means of pressure treatment or vacuum impregnation. These compositions may also be incorporated into a fish net fiber during manufacture.

Marine coatings comprise a binder and solvent and optionally other ingredients. The solvent may be either organic solvent or water. The marine antifouling agents of the invention are suitable for use in both solvent and water based marine coatings. Solvent based marine coatings are preferred.

Any conventional binder may be utilized in the marine antifouling coating incorporating one or more of the antifouling agents of the invention. Suitable binders include, but are not limited to: polyvinyl chloride in a solvent based system; chlorinated rubber in a solvent based system; acrylic resins in solvent based or aqueous systems; vinyl chloride-vinyl acetate copolymer systems as aqueous dispersions or solvent based systems; butadiene-styrene rubbers; butadiene-acrylonitrile rubbers; butadiene-styrene-acrylonitrile rubbers; drying oils such as linseed oil; asphalt; epoxies; siloxanes; and the like.

The marine coatings of the present invention may optionally contain one or more of the following: inorganic pigments, organic pigments, or dyes, and controlled release materials, such as rosin. Water based coatings may also optionally contain: coalescents, dispersants, surface active agents, rheology modifiers, or adhesion promoters. Solvent based coatings may also optionally contain extenders, plasticizers, or rheology modifiers.

A typical marine coating comprises 2 to 20% wt binders, 0 to 15% wt rosins/modified rosins, 0.5 to 5% wt plasticizers, 0.1 to 2% wt antisettling agent, 5 to 60% wt solvent/diluent, 0 to 70% wt cuprous oxide, 0 to 30% wt pigments (other than cuprous oxide), and 0 to 15% wt marine antifouling agent.

Coatings containing the marine antifouling agents of the invention may be applied to a structure to be protected by any of a number of conventional means. Suitable means of application include, but are not limited to, spraying; rolling; brushing; or dipping.

It is known in the art that the performance of marine antifouling agents may be enhanced by combination with one or more other marine antifouling agents. Thus, other known marine antifouling agents may be combined advantageously with the marine antifouling agents of this invention. The compounds of this invention may be combined with, e.g., tin based marine antifoulants. Such a combination has the advantage of reducing the amount of tin used and thereby lessening the amount of tin in the environment. Other marine antifouling agents useful in combination with the compounds of the invention include, but are not limited to, manganese ethylenebisdithiocarbamate; zinc dimethyl dithiocarbamate; 2-methyl-4-t-butylamino-6-cyclopropylamino-s-triazine; 2,4,5,6-tetrachloroisophthalonitrile; N,N-dimethyl dichlorophenyl urea; zinc ethylenebisdithiocarbamate; copper thiocyanate; 4,5-dichloro-2-n-octyl-3-isothiazolone; N-(fluorodichloromethylthio)phthalimide; N,N-dimethyl-N'-phenyl-N'-fluorodichloromethylthio-sulfamide; zinc 2-pyridinethiol-1-oxide; tetramethylthiuram disulfide; copper-10% nickel alloy solid solution; 2,4,6-trichlorophenylmaleimide; 2,3,5,6-tetrachloro-4-(methylsulfonyl)-pyridine; 3-iodo-2-propynyl butyl carbamate; diiodomethyl p-tolyl sulfone; bis dimethyl dithiocarbamoyl zinc ethylenebisdithiocarbamate; phenyl (bispyridil) bismuth dichloride; 2-(4-thiazolyl)- benzimidazole; pyridine triphenyl borane; phenylamides; halopropargyl compounds; or 2-haloalkoxyaryl-3-isothiazolones. Suitable 2-haloalkoxyaryl-3-isothiazolones include, but are not limited to, 2-(4-trifluoromethoxyphenyl)-3-isothiazolone, 2-(4-trifluoromethoxyphenyl)-5-chloro-3-isothiazolone, and 2-(4-trifluoromethoxyphenyl)-4,5-dichloro-3-isothiazolone.

The compounds of the invention are also useful as microbicides in controlling or inhibiting the growth of microorganisms, such as bacteria and fungi, in a locus.

When used as microbicides, the compounds of the invention can either be added directly to the locus to be protected or added as a composition comprising one or more of the compounds of the invention in a suitable carrier. Suitable carriers useful for microbicidal applications include, but are not limited to, water; organic solvent, such as ethylene glycol, diethylene glycol, propylene glycol, dipropylene glycol, xylene, toluene, or esters; or mixtures thereof The compounds of the invention are suitable for use in any locus requiring protection from microorganisms. Examples of loci where the compounds of the invention may be used include, but are not limited to, cooling towers; air washers; pulp and paper processing fluids; adhesives; caulks; mastics; sealants; agriculture adjuvant preservation; construction products; cosmetics and toiletries; shampoos; disinfectants and antiseptics; emulsions and dispersions; formulated industrial and consumer products; laundry rinse water; leather and leather products; lubricants; hydraulic fluids; medical devices; metalworking fluids; odor control fluids; paints; latexes; coatings; petroleum processing fluids; fuel; oil field fluids; photographic chemicals; printing fluids; sanitizers; soaps; detergents; textiles; and textile products.

When used as microbicides, the amount of the pyridazinone or dihydropyridazinone compounds of the invention necessary to control or inhibit the growth of microorganisms depends upon the locus to be protected, but is typically from 0.5 to 2000 ppm based on the locus to be protected. For example, a locus such as a metal working fluid may require 5 to 50 ppm of the compounds of the invention to control or inhibit microorganism growth where a locus such as paint may require 1000 to 2000 ppm.

It is known in the art that the performance of microbicides may be enhanced by combination with one or more other microbicides. Thus, other known microbicides may be combined advantageously with the microbicides of this invention. Microbicides useful in combination with the microbicides of the present invention include, but are not limited to, 5-chloro-2-methyl-3-isothiazolone, 2-methyl-3-isothiazolone, 2-n-octyl-3-isothiazolone, 4,5-dichloro-2-n-octyl-3-isothiazolone, iodopropargyl butylcarbamate, 1,2-dibromo-2,4-dicyanobutane, methylene-bis-thiocyanate, 2-thiocyanomethylthiobenzothiazole, tetrachloroisophthalonitrile, 5-bromo-5-nitro-1,3-dioxane, 2-bromo-2-nitropropanediol, 2,2-dibromo-3-nitrilopropionamide, N,N'-dimethylhydroxyl-5,5'-dimethylhydantoin, bromochlorodimethylhydantoin, 1,2-benzisothiazolin-3-one, and 4,5-trimethylene-2-methyl-3-iosthiazolone. Combinations of the microbicides of the present invention with 5-chloro-2-methyl-3-isothiazolone, 2-methyl-3-isothiazolone, 2-n-octyl-3-isothiazolone, 4,5-dichloro-2-n-octyl-3-isothiazolone, and mixtures thereof are preferred.

The following examples are presented to illustrate further various aspects of the present invention, but are not intended to limit the scope of the invention in any aspect.

EXAMPLE 1

Tests were conducted to determine the toxicity of the marine antifouling agents of the invention to Amphora. Amphora are indicative of soft fouling organisms.

*Amphora coffeaeformis* var. perpusilla was isolated from a natural biofilm and cultured axenically in Guillard's F2 medium. A log phase culture of Amphora was diluted with F2 medium to give a chlorophyll α concentration of 0.25 μg/mL. Chlorophyll α was measured by passing a measured volume (FV) of cell culture through a 3 μm pore, 25 mm diameter cellulose nitrate filter. The filter plus trapped algal cells was transferred to a glass tube. A measured volume (SV) of DMSO solvent was added to the glass tube. The tubes were incubated for 1.5 hours in darkness. After incubation, the absorbance of the sample was read in a spectrophotometer at 630 and 664 nm against a DMSO/filter blank. The chlorophyll a concentration can be calculated using the following equation:

$$\text{Chlorophyll } \alpha \text{ } (\mu g/mL) = 11.47 \times Abs_{664} - 0.4 \times Abs_{630} \times SV/FV$$

Ten mL of the diluted culture was pipetted into glass tubes. Ten μL of marine antifouling agent or, in the case of controls, DMF was added to each glass tube. The tubes were incubated on an illuminated orbital shaker at 20° C. for 96 hours before the chlorophyll α concentration of each tube was measured. Three replicates of each treatment were used. The effects of marine antifouling agents are calculated as % inhibition of the mean control. The $EC_{50}$ is the dose effective at preventing 50% growth. The $EC_{100}$ is the dose effective at preventing 100% growth. Results of the tests are shown in Table 1.

Activity Against *Amphora coffeaeformis* var. perpusilla

| Compound | $EC_{50}$ | $EC_{100}$ |
| --- | --- | --- |
| 1 | 8 | 20 |
| 2 | >20 | >20 |
| 3 | 5 | 10 |
| 4 | >20 | >20 |
| 5 | 5 | 20 |
| 6 | >20 | >20 |

Compounds showing activity against Amphora in the low ppm range are considered active against soft fouling organisms. These results demonstrate the compounds of this invention are efficacious against soft fouling organisms in low concentrations.

EXAMPLE 2

Tests were conducted to determine the toxicity of the marine antifouling agents of the invention to Artemia. Artemia are indicative of hard fouling organisms.

Substitute ocean water was prepared following ASTM Method D 1141-90. The water was sterilized by filtration through a 0.22 micron cellulose acetate membrane filter. San Francisco Bay Brand® *Artemia salina* cysts were purchased from a local aquarium supply store. The cysts were hatched in a 250 mL Erlenmeyer flask. The Artemia cysts (0.2 g) were weighed into a sterilized flask. One hundred mL of sterile ASTM sea water was added to the flask. The flask was placed on an orbital shaker set at approximately 150 rotations per minute and 28° C. After 24 hours, the contents of the flask were poured into a separatory funnel. The egg shells were separated from the *Artemia nauplii* (larvae), as the shells floated to the top. The nauplii were returned to the flask for another 24 hours shaking. The inoculum was prepared by pouring the nauplii into a crystallizing dish 48 hours after the cysts were originally placed on the shaker. After the nauplii congregated, they were taken up in a sterile serological pipette and transferred into another crystallizing dish. The suspension was stirred with a magnetic stirrer enough to keep the nauplii in suspension. Eighty mL of sterile sea water was added to the suspension. Using an eight channel microliter pipetter loaded with wide bore pipette tips, 100 μL of the suspension was transferred into a column of a 96 well, flat bottom, tissue culture plate. The number of nauplii in 3 to 4 wells was counted under a microscope. The number was averaged, and the inoculum was adjusted through further dilution, to 25 to 30 nauplii per 100 mL.

Stock solutions of the compounds to be tested were prepared on a weight to volume basis. Stock solutions were prepared at 40 times the highest concentration to be tested. Solvents were chosen based on the solubility of the compound to be tested. Solvents used were DMSO, acetone, or isopropanol. The solvents were tested to make sure that they had no effect on the test results.

Ninety six well, flat bottom, tissue culture plates were used for these tests.

One hundred ninety μL of sterile ASTM sea water was added to column 1 of each plate. One hundred μL of sterile ASTM sea water was added to columns 2 through 12 of each plate. Ten μL of a stock solution of one compound to be tested was added to the first three wells of column 1. The next 2 wells were skipped, as they serve as untreated controls. Ten μL of a stock solution of a second compound to be tested was added to the last three wells of column 1. Serial dilutions were performed by mixing and transferring 100 μL from column 1 to column 2, then from column 2 to 3, and the process was continued until all 12 columns were diluted. One hundred μL from column 12 was discarded. One hundred μL of the stirring Artemia inoculum was added to each well of the plate. The test plate was covered with a plastic tissue culture plate lid and incubated for 24 hours at 25° C.

Plates were read under a low magnification microscope 24 and 48 hours after the nauplii were added to the plate. The highest dilution in which all of the nauplii are dead is the $LC_{100}$. Nauplii are considered alive if any movement is seen during the viewing period. Results of this test are shown in Table 2.

Artemia LC 100 (ppm)

| Compound | 24 Hours | 48 Hours |
|---|---|---|
| 1 | 2.5 | 1 |
| 2 | 2.5 | 2.5 |
| 3 | 2.5 | 1 |
| 4 | 10 | 5 |
| 5 | 1 | 0.5 |
| 6 | 5 | 2.5 |

Compounds showing activity against Artemia in the low ppm range are considered active against hard fouling organisms. These results demonstrate that the compounds of this invention are efficacious against hard fouling organisms.

What is claimed is:

1. A method of inhibiting the growth of marine organisms on a marine structure, comprising applying to, on, or in the marine structure a marine organism inhibiting amount of a marine antifouling agent of formula:

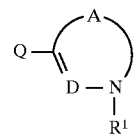

wherein:

A=—$(CHR^2)_n$—$CHR^7$—Z—; —$CR^2$=$CR^7$—Z—; $CHR^2$—$CR^7$=X—; or —$CR^2$=$CR^2$—X—;

D=nitrogen;

Q=an aromatic group selected from

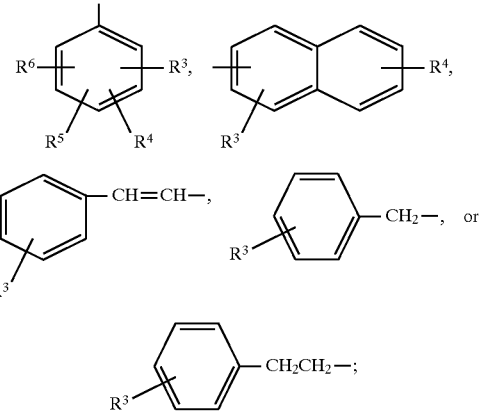

Z=a carbonyl or thiocarbonyl;

X=a carbon substituted by halo, alkoxy, alkynylthio, or triazolyl;

$R^1$=$(C_3-C_{10})$alkynyl, $(C_4-C_{20})$dialkynyl, halo$(C_3-C_6)$ alkynyl, phenyl$(C_3-C_6)$alkynyl, heterocyclyl$(C_3-C_6)$ alkynyl, $(C_3-C_6)$cycloalkyl$(C_3-C_6)$alkynyl, $(C_3-C_6)$ alkenyl$(C_3-C_6)$alkynyl, hydroxy$(C_3-C_6)$alkynyl, $(C_1-C_6)$alkoxy$(C_3-C_6)$alkynyl, $(C_1-C_6)$alkanoyloxy $(C_3-C_6)$alkynyl, formyl$(C_3-C_6)$alkynyl, tri$(C_1-C_6)$ alkylsilyl$(C_3-C_6)$alkynyl, halo$(C_3-C_6)$alkenyl$(C_3-C_6)$ alkynyl, carboxy$(C_3-C_6)$alkynyl, $(C_1-C_6)$ alkoxycarbonyl$(C_3-C_6)$alkynyl;

$R^2$=hydrogen, $(C_1-C_3)$alkyl, phenyl, or halogen;

$R^3$ and $R^6$ are independently hydrogen, $(C_1-C_6)$alkoxy, or halogen;

$R^2$ and $R^3$ may together form a $(C_1-C_3)$alkyl;

$R^4$=hydrogen, halogen, $(C_1-C_6)$alkoxy, or nitro;

$R^5$=hydrogen, halogen, nitro, $(C_1-C_6)$alkyl, $(C_1-C_6)$ alkoxy, $(C_1-C_6)$alkylthio, halo$(C_1-C_6)$alkyl, halo $(C_1-C_6)$alkoxy, halo$(C_1-C_6)$alkylthio, phenyl, phenoxy, or cyano;

$R^7$=hydrogen, $(C_1-C_3)$alkyl, phenyl, halogen, $(C_3-C_6)$ alkynyl$(C_2-C_6)$alkenyl, $(C_3-C_{10})$alkynyl, $(C_4-C_{20})$ dialkynyl, halo$(C_3-C_6)$alkynyl, or $(C_3-C_6)$alkenyl $(C_3-C_6)$alkynyl;

$R^2$ and $R^7$ may together form a fused phenyl ring; and n=1.

2. A method according to claim 1 wherein $R^1$ is $(C_3-C_{10})$ alkynyl, halo$(C_3-C_6)$alkynyl, or $(C_3-C_6)$alkenyl$(C_3-C_6)$ alkynyl.

3. A method according to claim 2 wherein the marine antifouling agent is selected from one or more of the group consisting of 6-(4-chlorophenyl)-2-(2'-pentynyl)pyridazin-3-one; 6-(4-chlorophenyl)-2-(2'-pentynyl)-4,5-dihydropyridazin-3-one; 6-(4-chlorophenyl)-2-(3'-vinyl-2'- propynyl)pyridazin-3-one; 7-chloro-2,4,4a,5-tetrahydro-2-(2-pentyn-1-yl)-indeno(1,2-c)-pyridazin-3-one; 6-(3-fluoro-4-chlorophenyl)-2-(2'-pentynyl)pyridazin-3-one; and 6-(4-chlorophenyl)-2-(5'-fluoro-2'-pentynyl)pyridazin-3-one.

4. A method according to claim 1 wherein the marine antifouling agent is incorporated in a carrier or a marine coating.

5. A method according to claim 4 wherein the amount of the marine antifouling agent in the carrier or coating is from 0.1 to 30% wt based on the weight of the structure to be protected or based on the weight of the coating to be applied.

6. A method of inhibiting the growth of marine organisms on a marine structure comprising applying to, on or in the marine structure a marine organism inhibiting amount of a combination of a first marine antifouling agent of the formula

(I)

wherein:
A=—$(CHR^2)_n$—$CHR^7$—Z; —$CR^2$=$CR^7$—Z—; $CHR^2$—$CR^7$=X—; or —$CR^2$=$CR^2$—X—;
D=nitrogen,
Q=an aromatic group selected from

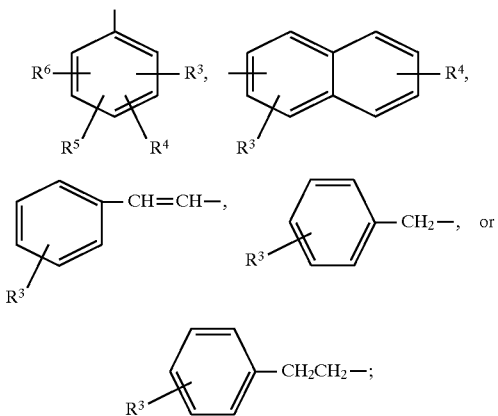

Z=a carbonyl or thiocarbonyl;
X=a carbon substituted by halo, alkoxy, alkynylthio, or triazolyl;
$R^1$=($C_3$–$C_{10}$)alkynyl, ($C_4$–$C_{20}$)dialkynyl, halo($C_3$–$C_6$)alkynyl, phenyl($C_3$–$C_6$)alkynyl, heterocyclyl($C_3$–$C_6$) alkynyl, ($C_3$–$C_6$)cycloalkyl($C_3$–$C_6$)alkynyl, ($C_3$–$C_6$)alkenyl($C_3$–$C_6$)alkynyl, hydroxy($C_3$–$C_6$)alknyl, ($C_1$–$C_6$)alkoxy($C_3$–$C_6$)alkynyl, ($C_1$–$C_6$)alkanoyloxy ($C_3$–$C_6$)alkynyl, formyl($C_3$–$C_6$)alkynyl, tri($C_1$–$C_6$) alkylsilyl($C_3$–$C_6$)alkynyl, halo($C_3$–$C_6$)alkenyl($C_3$–$C_6$) alkynyl, carboxy($C_3$–$C_6$)alkynyl, ($C_1$–$C_6$) alkoxycarbonyl($C_3$–$C_6$)alkynyl;

$R^2$=hydrogen, ($C_1$–$C_3$)alkyl, phenyl, or halogen;

$R^3$ and $R^6$ are independently hydrogen, ($C_1$–$C_6$)alkoxy, or halogen;

$R^2$ and $R^3$ may together form a ($C_1$–$C_3$)alkyl;

$R^4$=hydrogen, halogen, ($C_1$–$C_6$)alkoxy, or nitro;

$R^5$=hydrogen, halogen, nitro, ($C_1$—$C_6$)alkyl, ($C_1$–$C_6$) alkoxy, ($C_1$–$C_6$)alkylthio, halo($C_1$–$C_6$)alkyl, halo ($C_1$–$C_6$)alkoxy, halo($C_1$–$C_6$)alkylthio, phenyl, phenoxy, or cyano;

$R^7$=hydrogen, ($C_1$–$C_3$)alkyl, phenyl, halogen, ($C_3$–$C_6$) alkynyl($C_2$–$C_6$)alkenyl, ($C_3$–$C_{10}$)alkynyl, ($C_4$–$C_{20}$) dialkynyl, halo($C_3$–$C_6$)alkynyl, or ($C_3$–$C_6$)alkenyl ($C_3$–$C_6$)alkynyl;

$R^2$ and $R^7$ may together form a fused phenyl ring; n=1;

and a second marine antifouling agent selected from the group consisting of: tin based marine antifoulants; manganese ethylenebisdithiocarbamate; zinc dimethyl dithiocarbamate; 2-methyl-4-t-butylamino-6-cyclopropylamino-s-triazine; 2,4,5,6-tetrachloroisophthalonitrile; N,N-dimethyl dichlorophenyl urea; zinc ethylenebisdithiocarbamate; copper thiocyanate; 4,5-dichloro-2-n-octyl-3-isothiazolone; N-(fluorodichloromethylthio)-phthalimide; N,N-dimethyl-N'-phenyl-N'-fluorodichloromethylthio-sulfamide; zinc 2-pyridinethiol-1-oxide; tetramethylthiuram disulfide; copper-10% nickel alloy solid solution; 2,4,6-trichlorophenylmaleimide; 2,3,5,6-tetrachloro-4-(methylsulfonyl)-pyridine; 3-iodo-2-propynyl butyl carbamate; diiodomethyl p-tolyl sulfone; bis dimethyl dithiocarbamoyl zinc ethylenebisdithiocarbamate; phenyl (bispyridil) bismuth dichloride; 2-(4-thiazolyl)-benzimidazole; pyridine triphenyl borane; and 2-haloalkoxyaryl-3-isothiazolones; wherein the ratio of the first marine antifouling agent to the second marine antifouling agent is from 99:1 to 1:99.

7. A method according to claim 1 wherein the marine structure is selected from the group consisting of boats, oil platforms, piers, pilings, docks, and fish nets.

* * * * *